US00PP21843P3

(12) United States Plant Patent
Bourne

(10) Patent No.: US PP21,843 P3
(45) Date of Patent: Apr. 5, 2011

(54) ***DIANTHUS* PLANT NAMED 'WP09 WEN04'**

(50) Latin Name: *Dianthus×hybrida*
Varietal Denomination: WP09 WEN04

(76) Inventor: Carolyn Grace Bourne, Dawlish (GB)

( * ) Notice: Subject to any disclaimer, the term of this patent is extended or adjusted under 35 U.S.C. 154(b) by 0 days.

(21) Appl. No.: 12/660,862

(22) Filed: Mar. 4, 2010

(65) Prior Publication Data

US 2010/0229269 P1 Sep. 9, 2010

(51) Int. Cl.
*A01H 5/00* (2006.01)

(52) U.S. Cl. ..... Plt./281

(58) Field of Classification Search ..... Plt./281
See application file for complete search history.

*Primary Examiner* — Annette H Para

(57) ABSTRACT

A new cultivar of *Dianthus* plant named 'WP09 WEN04' which is characterized by compact plant habit and fragrant semi-double flowers which are predominantly salmon-pink in color, with a carmine colored eye. In combination, these characteristics set 'WP09 WEN04' apart from all other existing varieties of *Dianthus* known to the inventor.

2 Drawing Sheets

Genus: *Dianthus.*
Species: ×*hybrida.*
Denomination: 'WP09 WEN04'.

BACKGROUND OF THE INVENTION

This application claims the benefit of priority under 35 U.S.C. 119(f) of the application for a grant of European Community Plant Breeders Rights which was filed for the instant plant variety on Mar. 9, 2009, Application Number 2009/0419.

The present invention relates to a new and distinct cultivar of hardy garden pink or carnation that is grown for use as a flowering plant for pots and containers and for planting in the garden and landscape. The new cultivar is known botanically as *Dianthus×hybrida* and will be referred to hereinafter by the cultivar name 'WP09 WEN04'.

'WP09 WEN04' is a complex hybrid plant that is the product of a breeding program started by the inventor in 1985. The breeding program is conducted in a cultivated area of Houndspool, Dawlish, Devon, United Kingdom. The inventor selected 'WP09 WEN04' in 2004 for its fragrant flowers which are semi-double and predominantly salmon-pink in color, with a carmine colored eye.

'WP09 WEN04' resulted from the controlled pollination between two unreleased and unpatented selections of *Dianthus* from the inventor's breeding program, namely Selection "XIN 02.07" as male parent and Selection "BEL 03.07" as female parent.

'WP09 WEN04' is distinguishable from the male parent as follows: The flowers of the male parent are semi-double and magenta in color, with a dark magenta eye, whereas the flowers of 'WP09 WEN04' are semi-double and predominantly salmon-pink in color, with a carmine colored eye.

'WP09 WEN04' is distinguishable from the female parent as follows: The female plant is vigorous and produces tall plants with long flower stems, typically 30 cm-40 cm in length, whereas the flower stems of 'WP09 WEN04' are 15 cm-20 cm in length.

The variety of *Dianthus* which is considered by the inventor to most closely resemble 'WP09 WEN04' is *Dianthus* 'Doris' (unpatented). 'Doris' is similarly semi-double and salmon-pink in color. However, 'Doris' is a vigorous variety and exhibits greater overall plant size, longer flower stems and larger flowers than 'WP09 WEN04'.

Asexual reproduction of 'WP09 WEN04' was first accomplished by the inventor in 2004 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP09 WEN04'. These traits in combination distinguish this cultivar from all other commercial varieties known to the inventor. 'WP09 WEN04' has not been tested under all possible conditions and phenotypic differences may be observed with variations in environmental, climatic and cultural conditions, however, without any variance in genotype.

1. *Dianthus* 'WP09 WEN04' exhibits a compact habit.
2. The flowers of *Dianthus* 'WP09 WEN04' are semi double.
3. The flowers of *Dianthus* 'WP09 WEN04' are predominantly salmon-pink in color, with a carmine colored eye.
4. *Dianthus* 'WP09 WEN04' blooms from April through October.
5. *Dianthus* 'WP09 WEN04' exhibits grey-green foliage.
6. At nine months of age, the height of the foliage mound of *Dianthus* 'WP09 WEN04' is 20 cm to 25 cm, and the width is 18 cm to 20 cm.
7. *Dianthus* 'WP09 WEN04' is perennial and is hardy to −15° C.
8. *Dianthus* 'WP09 WEN04' is suitable for use as a flowering plant in pots and containers.

BRIEF DESCRIPTION OF THE DRAWINGS

The accompanying color drawings illustrate the overall appearance of the new *Dianthus* variety 'WP09 WEN04' showing colors as true as it is reasonably possible to obtain in colored reproductions of this type. Colors in the drawings may differ from the color values cited in the detailed botanical description, which accurately describe the actual colors of the new variety 'WP09 WEN04'.

The drawing labeled as FIG. 1 depicts an entire flowering plant.

Figure 1:
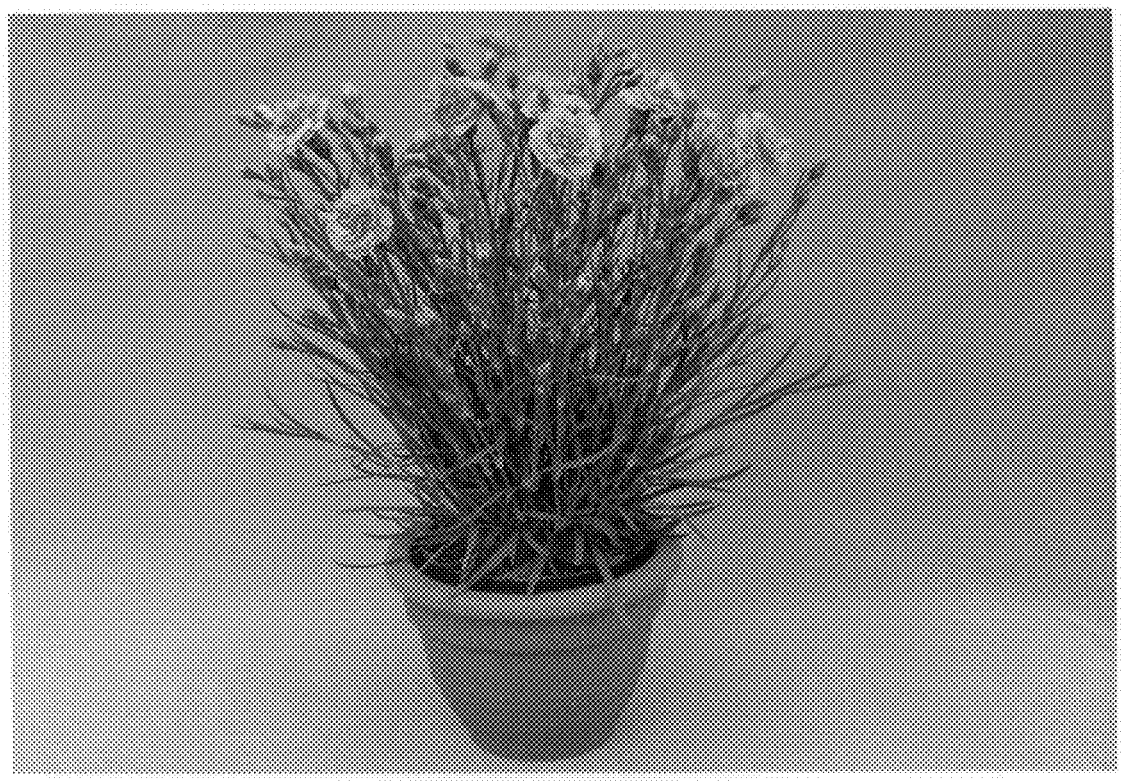
Figure 2:
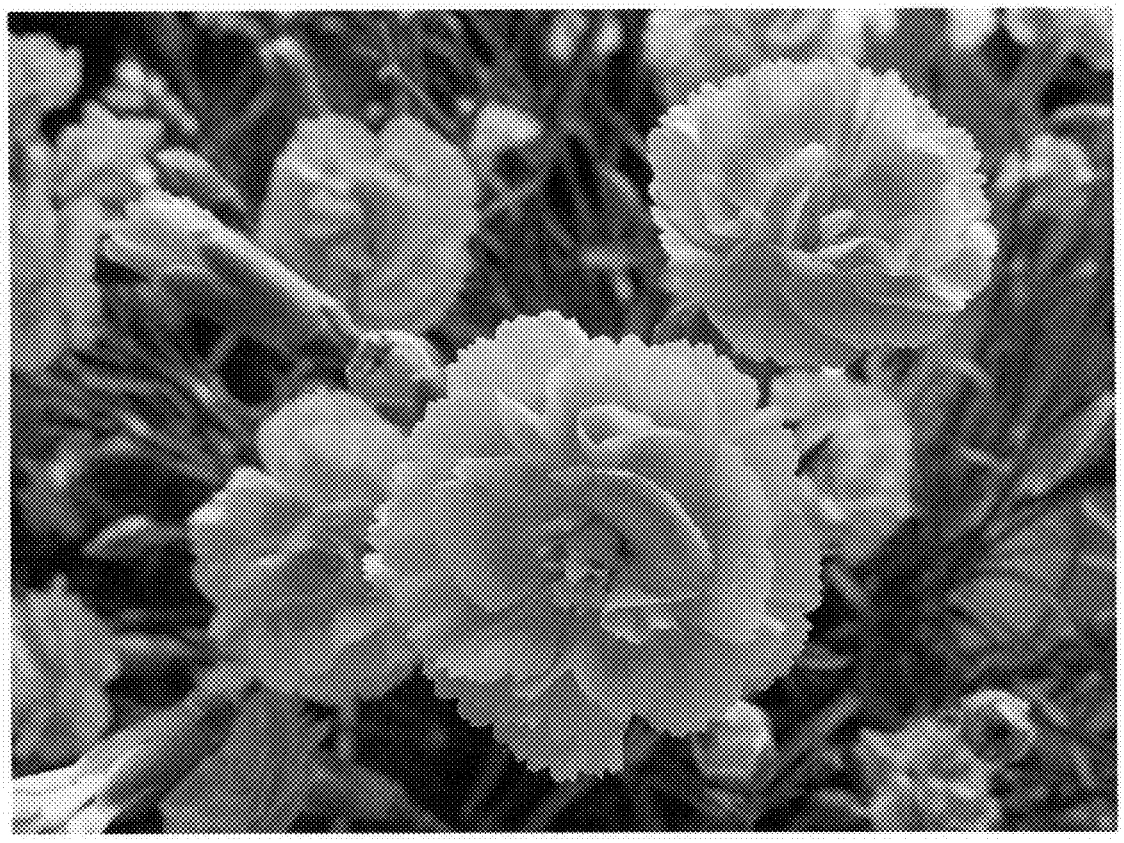

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP09 WEN04'. Data was collected in spring from 1.5-liter container plants in spring, and grown indoors in Devon, United Kingdom. The color determinations are in accordance with the 2002 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:

Family: Caryophyllaceae.

Genus: *Dianthus*.

Species: ×*hybrida*.

Denomination: 'WP09 WEN04'.

Parentage: A complex *Dianthus* hybrid whose immediate parents are unreleased hybrids from the inventor's breeding program, identified as follows:

Male parent: Unpatented selection of *Dianthus* from the inventor's breeding program, known as Selection "XIN 02.07".

Female parent: Unpatented selection of *Dianthus* from the inventor's breeding program, known as Selection "BEL 03.07".

Plant type: Flowering perennial.

Use of plant: As a flowering plant in containers, window boxes, planters, pots and the garden.

Bloom period: April-October in Devon, UK.

Plant habit: A compact mound with many branches and stems upright.

Height of plant: 20 cm to 25 cm after 9 months.

Width of plant: 18 cm to 20 cm after 9 months.

Hardiness: Has survived in temperatures of minus 15 Centigrade, equivalent to USDA Hardiness Zone 7.

Root system: Many fibrous roots.

Propagation method: Vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: Mist propagation unit is required for satisfactory rooting of cuttings.

Crop time: 3 months starting in the Spring and 6 months starting in the Fall.

Plant stem:

*Shape.*—Cylindrical.

*Height.*—10 cm to 12 cm.

*Diameter.*—3 mm to 4 mm.

*Surface.*—Glabrous and glaucous.

*Color.*—145C.

*Branching.*—Numerous shoots from the axils of the lower leaves.

*Internode length* (*between nodes*).—6 mm to 10 mm.

Leaf:

*Type.*—Evergreen.

*Shape.*—Linear, straight.

*Division.*—Simple.

*Apex.*—Acute.

*Base.*—Decurrent.

*Venation.*—Not prominent.

*Margins.*—Entire.

*Arrangement.*—Opposite and spiraling on stem.

*Attachment.*—Sheathing.

*Surface adaxial.*—Glaucous.

*Surface abaxial.*—Glaucous.

*Fragrance.*—Absent.

*Dimensions.*—Length: 100 mm to 150 mm. Width: 4 mm to 5 mm.

*Color.*—Adaxial surface: 189A. Abaxial surface: N138B.

Inflorescence:

*Flower stem.*—Length: 150 mm to 200 mm. Width: 3 mm. Stem strength: Erect. Stem color: 189B.

*Inflorescence.*—Cymose.

*Type.*—Salviform, symmetrical.

*Development.*—Singly, in sequence from the uppermost bud.

Buds:

*Shape.*—Conical.

*Dimensions.*—15 mm in length and 10 mm in diameter.

*Color.*—143B except apex, 150A.

*Surface texture.*—Glabrous.

Flowers:

*Number.*—5 to 7 per stem.

*Pedicel dimensions.*—180 mm to 200 mm in length and 2 mm to 3 mm in width.

*Pedicel strength.*—Erect.

*Pedicel color.*—N189B.

*Flower dimensions.*—Length (including calyx): 40 to 45 mm. Diameter: 45 to 50 mm.

*Flower shape.*—Circular.

*Flower profile.*—Convex for the upper part of the corolla and concave for the lower part of the corolla.

*Lastingness.*—8 days at 20° C., on the plant.

*Fragrance.*—Medium perfume.

*Flowering period.*—April to October, in Devon, UK.

Corolla:

*Shape* (*upper part of corolla*).—Convex.

*Shape* (*lower part of corolla*).—Concave.

*Petal arrangement.*—Persistent, apopetalous, overlapping.

*Petal margin.*—Dentate.

*Indentation.*—Varies between 0 mm and 1 mm.

*Petal texture.*—Soft.

*Flower type.*—Semi-double.

*Petal number.*—20 to 25 true petals.
*Petal dimension.*—Length: 41 mm to 43 mm. Width: 27 mm to 30 mm.
*Color pattern.*—Self with very light middle belt picotee type.
*Color of upper surface.*—Ground color of blade: 52C to 52D. Color of band across blade: Middle belt, picotee type, 52B. Color of middle of strap: 145C. Color of base of strap: 145D.
*Color of lower surface.*—Ground color of blade: 52C. Color of band across blade: No band. Color of middle of strap: 145C. Color of base of strap: 145D.
*Petal shape.*—Obdeltoid.
*Petal apex.*—Rounded, slightly flattened.
*Petal base.*—Tapers to narrow base, width at base 2 mm.
*Petal surface.*—Glabrous.

Calyx:
*Shape.*—Cylindrical.
*Sepal apex.*—Acuminate.
*Sepal base.*—Cuneate.
*Longitudinal profile.*—Flat.
*Dimensions.*—Length: 22 mm. Diameter: 10 mm.
*Sepals.*—Fused.
*Sepals number.*—5.
*Sepals color.*—143B on the top of the calyx and 144A or 144B on the base.
*Anthocyanin.*—Absent.
*Splitting.*—Not observed.

Epicalyx:
*Bracts number.*—1 pair of two.
*Shape of outer lobe.*—Acuminate.
*Dimensions.*—Width: 8 mm to 9 mm. Length: 10 mm to 12 mm.
*Color.*—N138B on the top and 144B on the base and the sides.
*Anthocyanin.*—Absent.

Bracteoles:
*Number.*—1 pair of two.
*Dimensions.*—Width: 12 mm. Length: 12 mm.
*Color.*—N138B on the tip and 145A or 145B on the margins and center.
*Anthocyanin.*—Absent.

Reproductive organs:
*Stamens.*—Number: From 0 to 5 stamens are petaloid (anther absent).
*Filaments.*—Number: 10 to 15. Color: White for lower three-fourths of the filament and 63C for the uppermost one-fourth. Dimensions: Length: 25 mm; diameter: 0.5 mm.
*Anthers.*—Number: 10 to 15 (excludes petaloid stamens). Color: 50D. Length: 4 mm; diameter: 1.5 mm. Attachment: Dorsifixed.
*Pollen.*—Present occasionally.
*Pollen color.*—N155A.
*Style.*—Number: 2. Shoulder: Absent. Color: White. Length: 20 mm to 25 mm. Width: 1 mm.
*Stigma.*—Number: Single. Color: No data, as all the style observed were immature. Dimensions: N/A.
*Ovary.*—Position: Superior. Dimensions: Length: 7 mm; diameter: 5 mm. Shape: Spindle. Color (upper surface): 145B. Color (lower surface): 145C.
*Seed.*—Seed has not been observed.

It is claimed:

1. A new and distinct cultivar of *Dianthus* plant named 'WP09 WEN04' as described and illustrated herein.

* * * * *